(12) United States Patent
Possum

(10) Patent No.: US 6,179,847 B1
(45) Date of Patent: Jan. 30, 2001

(54) TICK REMOVAL DEVICE

(76) Inventor: Jerry G Possum, 5 Miller Rd., Vernon, CT (US) 06066

( * ) Notice: Under 35 U.S.C. 154(b), the term of this patent shall be extended for 0 days.

(21) Appl. No.: 09/476,376

(22) Filed: Jan. 3, 2000

(51) Int. Cl.[7] .................................................. A61B 17/50
(52) U.S. Cl. ............................................................ 606/131
(58) Field of Search .................................. 606/211, 210, 606/131, 205, 206, 207, 9

(56) References Cited

U.S. PATENT DOCUMENTS 5,914,062 * 6/1999 Von Der Heyde ................... 606/210

* cited by examiner

Primary Examiner—Michael Buiz
Assistant Examiner—Vy Q. Bull

(57) ABSTRACT

A device for visually locating and safely removing a tick attached to a host, such as an animal or person, including small pets and children, while minimizing the possibility of leaving small tick parts embedded under the skin, that can result in infection, without the use of heated members or elements that could cause discomfort to the host. Such device incorporates a spot light to help locate and observe a tick as well as positive and negative electrodes formed as an elongated tweezer, having tips shaped to hold and squeeze a tick and a unique electrical circuit powered by two 1½ volt internal batteries, connected in series and controlled by a manually operated "ON" or "OFF" switch.

The device is held in one hand, with the tweezer between the thumb and forefinger. Either hand can be used. With the switch in the "ON" position, the spotlight is illuminated shining a light in front of the tweezer also, and the electrode tweezer is energized. The user locates the tick, squeezes it between the tips of the tweezer, which are formed to exert maximum pressure on the front end of the tick and automatically induces a small electric current to pass through the tick causing it to release its grip, the spot light will dim, indicating current flow, and the tick can be safely lifted off the skin of the host. The current flow through the tick is minimal and cannot be felt by a small pet or child.

1 Claim, 2 Drawing Sheets

TICK REMOVAL DEVICE

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of Search 219/227, 219/233, 219/229, 294/99.2, 294/100, 606/206, 606/131, 606/133, 606/264, 606/27, 606/29, 606/42, 606/210, 606/211, 362/157, 362/204, 362/202, 362/208, 362/119, 43/134

2. References Cited

| U.S. PATENT DOCUMENTS | | | |
|---|---|---|---|
| 3,200,028 | 8/1965 | Chisolm | 219/227 |
| 3,844,291 | 10/1974 | Moen | 606/206 |
| 3,938,527 | 2/1976 | Rioux et al. | 606/133 |
| 4,213,460 | 7/1980 | Weiner | 606/131 |
| 4,240,435 | 12/1980 | Yazawa et al. | 606/133 |
| 4,303,268 | 12/1981 | Davidson | 294/99.2 |
| 4,393,872 | 7/1983 | Reznik et al. | 604/294 |
| 4,442,837 | 4/1984 | Keatley | 606/131 |
| 4,979,771 | 12/1990 | Childs III | 294/99.2 |
| 5,002,232 | 3/1990 | Idsund | 294/100 |
| 5,035,695 | 7/1991 | Weber, Jr. et al | 606/42 |
| 5,250,046 | 10/1993 | Lee | 606/29 |
| 5,276,306 | 1/1994 | Huffman | 219/229 |
| 5,376,087 | 12/1994 | Riemann | 294/100 |
| 5,556,563 | 9/1996 | Heyde et al. | 219/227 |
| 5,565,122 | 10/1996 | Zinnbauer et al. | 219/227 |
| 5,690,847 | 11/1997 | Le Valley et al. | 219/233 |
| 5,914,062 | 6/1999 | Von Der Heyde | 294/99.2 |

3. Field of Invention

The device of this invention resides in the area of devices used to remove ticks from animals and people and, specifically, incorporates a spot light to locate and observe a tick, along with positive and negative electrodes formed as an elongated tweezer with unique tips to hold and squeeze the tick, as well as a unique electrical circuit powered by two internal 1½ volt batteries. When a tick is squeezed, a small amount of electric current automatically passes through the tick to cause it to release its grip on the skin of the host, the light will dim indicating current flow, the tick is then lifted off the skin with the tweezer, safely. The device does not use a heated element or member, which can cause discomfort to the host. The small amount of current that passes through the tick is so minimal that a small pet or child cannot feel it.

Explanation of Tick Removal, Concerns

A tick is any of numerous bloodsucking arachnids that attach themselves to warm blooded vertebrates to feed, and include important vectors of infectious diseases; some can transmit Lyme Disease to a host. They vary in size from approximately 0.100 inch in diameter to 0.300 inch in diameter and are difficult to visually locate. Once they attach themselves to the skin, they hold on and, if pulled off, will often leave some tick body parts embedded under the skin that can contribute to infection. The use of heat or heated tweezers to help induce the tick to release its grip on the skin of the host is not always practical, especially with small children or pet animals with long hair.

Description of the Prior Art

U.S. Pat. No. 4,213,460 to Weiner discloses forceps that are heated. U.S. Pat. No. 4,979,771 to Childs, III discloses cup members at the end of the tweezers to hold and remove a tick. U.S. Pat. No. 5,276,306 to Huffman indicates the use of a heated needle to insert into the tick, and a spoon member to remove the tick. U.S. Pat. No. 5,556,563 to Heyde et al. teaches heated tweezer arms that move together to grasp and heat the tick. U.S. Pat. No. 5,914,062 to Von Der Heyde discloses retractable tweezers that grip the tick, and provides a heated element near the tick to cause the tick to release its grip.

BRIEF SUMMARY OF THE INVENTION

It is the object of this invention to provide a safe and convenient hand-held, effective device to help locate, visually observe, and safely remove a tick attached to the skin of a host, such as an animal or person including small pets and children, while minimizing the possibility of leaving small tick parts embedded under the skin that can result in infection, without the use of heated members or elements that could cause discomfort to the host.

This invention incorporates a spot light to locate and observe a tick as well as a positive and negative electrode formed as an elongated tweezer, having the tips shaped to hold a tick, and a unique electrical circuit, powered by two each 1½ volt internal batteries, connected in series and controlled by a manually operated "ON" or "OFF" switch.

The device is held in one hand, either right or left as desired, with the electrode tweezer held between the thumb and forefinger, the same as one would hold a pencil.

With the switch in the "ON" position, the spot light is illuminated, projecting a beam of light in front of the tweezer, and the electrode tweezer is energized. The user locates the tick and carefully positions the tick between the electrode tweezer tips and squeezes the tick. The tips of the tweeezer are formed to apply maximum pressure on the front end of the tick. Automatically, a small amount of current will pass through the tick, and the spot light will dim, indicating current flow. The tick will relax its grip on the skin and allow the user to lift it safely off the host. The small amount of current that passes through the tick is so minimal that a small pet or child cannot feel it.

DETAILED DESCRIPTION OF THE INVENTION

Figure 1:
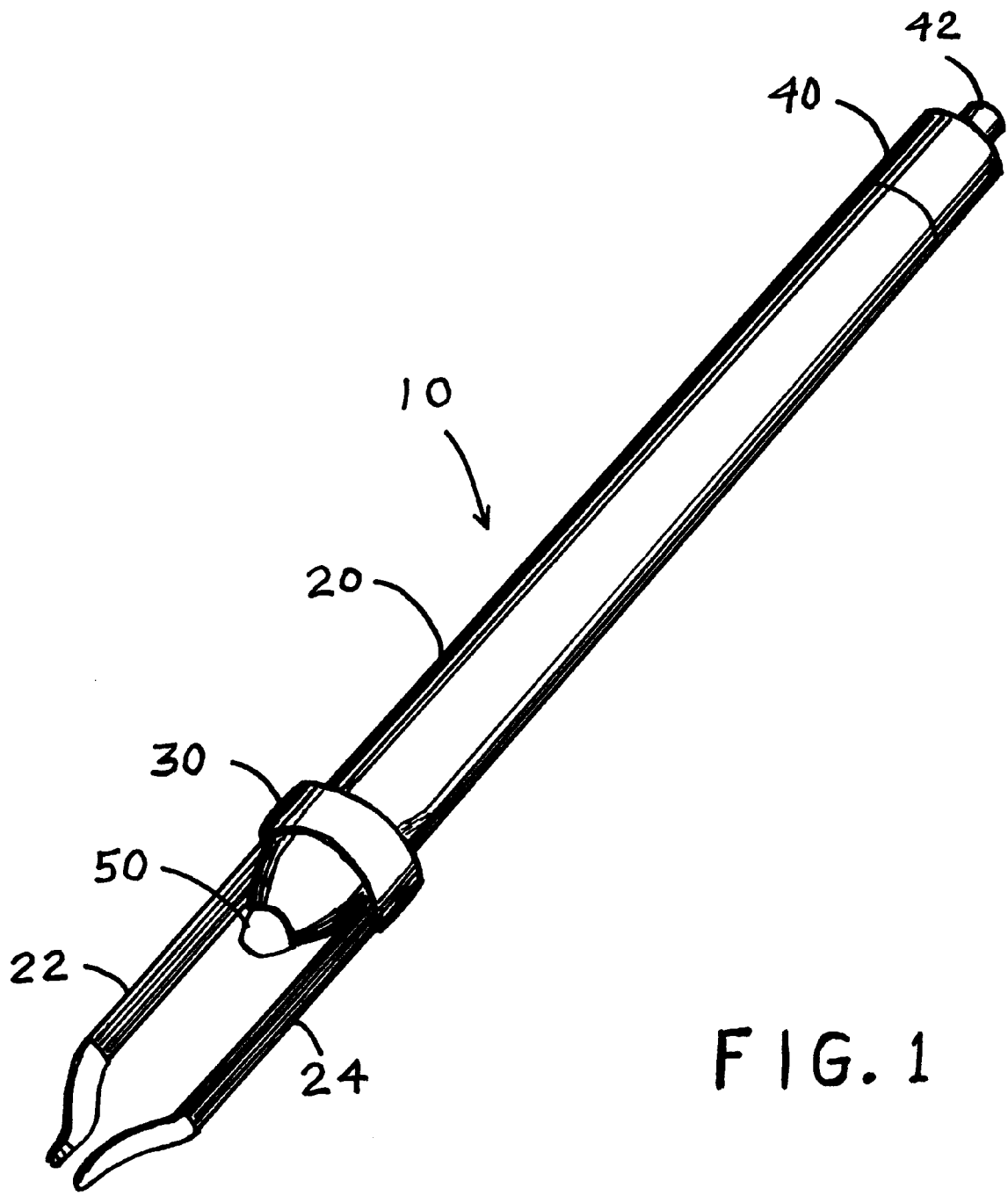
FIG. 1 illustrates the front perspective view of the device of this invention.
Figure 2:
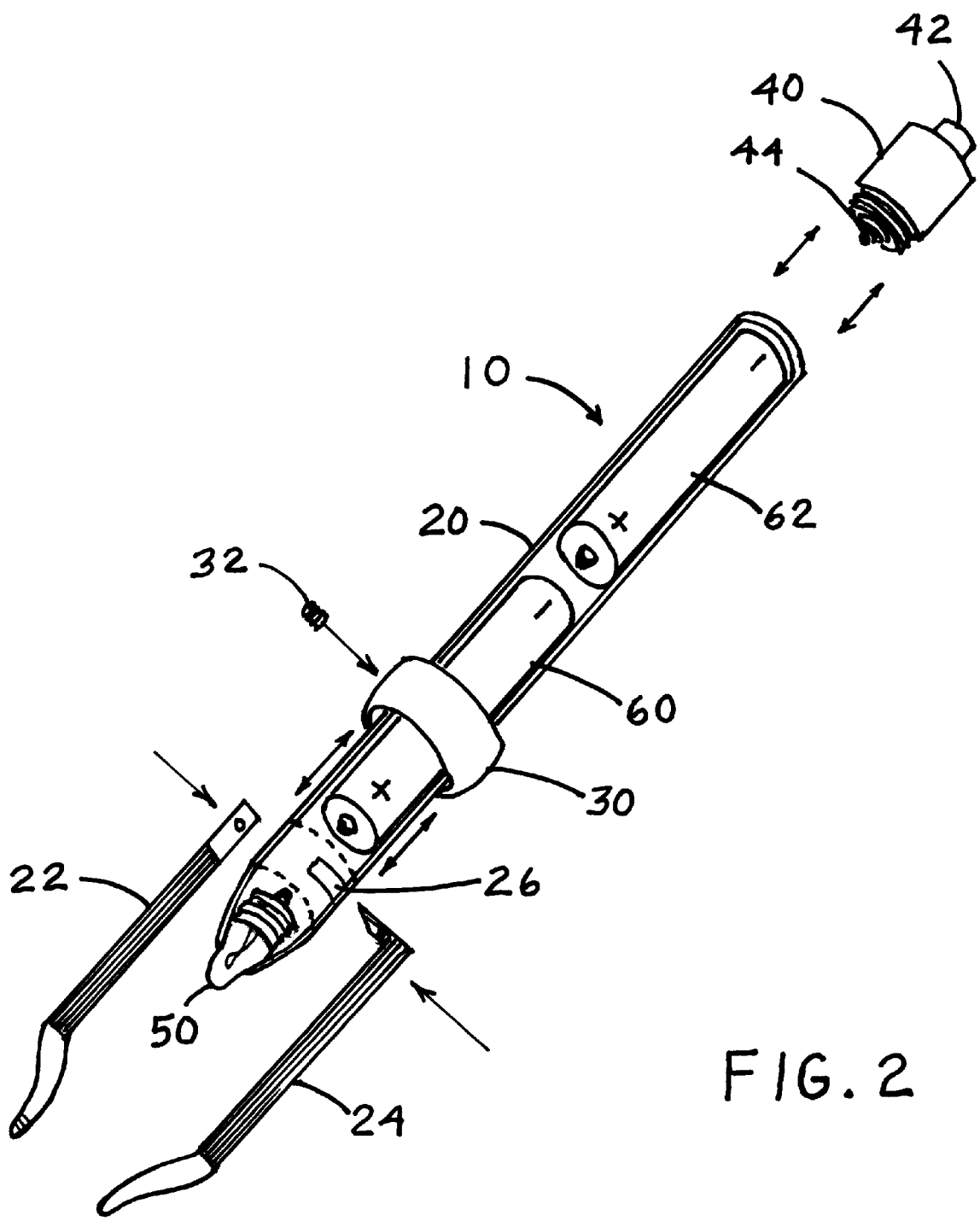
FIG. 2 illustrates a perspective view of the interior and individual components of this invention.

FIG. 1 illustrates a perspective view of the tick removal device 10 of this invention. The device consists of the main housing 20 that is tubular in shape and can be manufactured from metal, having an opening at the far end, to fit an end cap 40 that incorporates a manual "ON" or "OFF" switch 42 and a metal compression spring, and can be manufactured using plastic non-conductive materials. The front of housing 20 is tapered with a small opening to contain lamp 50 that is a standard 3-volt pen light lamp, and also electrodes 22 and 24 that form a tweezer. The electrodes can be manufactured by forming flat stainless alloy spring steel, having a thickness between 0.025 inch and 0.050 inch, a width between 0.100 inch and 0.300 inch, and a length between 2 and 4 inches. Electrodes 22 and 24 are electrically insulated in the shaded area as indicated in FIG. 1 and FIG. 2. The tips of electrodes 22 and 24 are shaped to hold a tick and apply maximum pressure on the front end of the tick when the tweezer is squeezed between the thumb and forefinger of the user. Ring 30 is made from plastic materials and is formed to hold electrodes 22 and 24 in place when positioned as shown in FIG. 1.

Referring to FIG. 2, lamp 50 is positioned inside housing 20 at the front end, where the side of the lamp's metal base contacts the metal housing. Negative electrode 22 is connected to the outside of housing 20 when ring 30 is in position and locked with setscrew 32 to assure a common connection with the metal housing. Positive electrode 24 is positioned through slot 26 in housing 20 making contact with the center contact of lamp 50; however, remaining electrically insulated from housing 20. Ring 30 is slipped into position holding electrodes 22 and 24 in place. Setscrew 32 locks ring 30 in place. Batteries 60 and 62 are 1½ volt each and are located inside housing 20, as indicated. End cap 40 is screwed onto housing 20 causing spring 44 to compress, forcing batteries 60 and 62 against the contact area of electrode 24 and the center contact of lamp 50. Switch 42, when in the "ON" position, connects the negative side of battery 62, by way of spring 44, to housing 20 that is common to negative electrode 22 and the base of lamp 50. Current flows from the negative side of battery 62 to the positive side of battery 62, to the negative side of battery 60 to the positive side of battery 60, to the contact point of lamp 50 through the lamp filament and back to housing 20, causing lamp 50 to illuminate and energizing positive electrode 24, with a 3 volt potential, ready for use. In this circuit the electrodes are in parallel with the lamp so that when current flows through the electrodes' tips when a tick is squeezed, the light will dim, giving the user an indication of current flow. The small amount of current that passes through the tick is so minimal a small pet or child cannot feel it. The device is held in either the right or left hand, as desired, with the electrode tweezer held between the thumb and forefinger. When the manual switch is in the "ON" position, a beam of light is projected in front of the tweezer, the user locates the tick on the host with the help of the spot light, positions the tick between the tweezer tips and squeezes the tick. The tips are formed to apply maximum pressure on the front end of the tick. The electrical circuit will automatically induce a small amount of direct current through the tick, the light will dim, indicating current flow, and in a few seconds the tick will release its grip and can be safely lifted off the skin of the host.

Although this invention has been described with reference to particular embodiments, it will be apparent to those skilled in the art that variations and modifications can be substituted therefor without departing from the principles and spirit of the invention.

What is claimed is:

1. A hand held device to locate and remove a tick attached to a host animal or person without the use of heated elements, comprising:

a tubular thin wall casing having an inwardly tapering front end, a rear end and an interior cavity defined therein, said casing having openings defined at the front end and the rear end;

a set of tweezer arms that are electrically insulated from said casing as defined, as well as electrically conductive, extending from the front end of said casing, attached to said casing by a locking ring that holds said tweezer arms in a fixed position on said casing so that said tweezer arms are disposed opposite one another and tapering inwardly toward one another, having shaped tips to hold a tick, when manually squeezed together;

a pen ligbtbulb located at the front end of said casing, positioned between said tweezer arms;

a battery power supply located within the internal cavity of said casing, that is controlled by a manual push button switch having an "on" and an "off" position, located at the rear end of said casing as part of an end cap, said manual push button switch controls an internal electrical circuit such that when in the "on" position said penlight bulb will shine a spotlight between said tweezer arm tips as well as energize said tweezer arm tips allowing a small electric current to pass through a tick held by said tweezer arm tips sufficient to cause said tick to release its grip on said host allowing said tick to be removed from said host, the light from said penlight bulb will dim when the current passes through said tick as an indication to the user.

\* \* \* \* \*